(12) United States Patent
Harris, Jr. et al.

(10) Patent No.: US 7,367,422 B2
(45) Date of Patent: May 6, 2008

(54) SYSTEM AND METHOD FOR PROVIDING PASSIVE NOISE REDUCTION

(75) Inventors: Kenneth David Harris, Jr., Hollis, NH (US); Vian W. Y. Li, Kowloon (HK); Baird M. Little, Nashua, NH (US)

(73) Assignee: Brookstone Purchasing. Inc., Merrimack, NH (US)

( * ) Notice: Subject to any disclaimer, the term of this patent is extended or adjusted under 35 U.S.C. 154(b) by 366 days.

(21) Appl. No.: 10/851,014

(22) Filed: May 21, 2004

(65) Prior Publication Data

US 2005/0257995 A1    Nov. 24, 2005

(51) Int. Cl.
*H04R 25/00* (2006.01)

(52) U.S. Cl. .................. 181/129; 181/137; 381/72; 381/74; 381/370

(58) Field of Classification Search .............. 181/29, 181/137; 381/72, 74, 370, 371, 372, 373, 381/374, 375, 376
See application file for complete search history.

(56) References Cited

U.S. PATENT DOCUMENTS

| | | | |
|---|---|---|---|
| 4,562,589 A | 12/1985 | Warnaka et al. | |
| 4,644,581 A | 2/1987 | Sapiejewski | |
| 4,654,871 A | 3/1987 | Chaplin et al. | |
| 4,833,719 A | 5/1989 | Carme et al. | |
| 4,922,542 A | 5/1990 | Sapiejewski | |
| 5,001,763 A | 3/1991 | Moseley | |
| 5,091,954 A | 2/1992 | Sasaki et al. | |
| 5,117,461 A | 5/1992 | Moseley | |
| 5,134,659 A | 7/1992 | Moseley | |
| 5,138,663 A | 8/1992 | Moseley | |
| 5,241,971 A * | 9/1993 | Lundin | 128/864 |
| 5,375,174 A | 12/1994 | Denenberg | |
| 5,381,473 A | 1/1995 | Andrea et al. | |
| 5,524,058 A | 6/1996 | Moseley | |
| 5,551,089 A * | 9/1996 | Whidden | 2/209 |
| 5,673,325 A | 9/1997 | Andrea et al. | |
| 5,691,515 A * | 11/1997 | Landis | 181/129 |
| 5,706,360 A * | 1/1998 | Khandekar | 381/370 |
| 5,715,321 A | 2/1998 | Andrea et al. | |
| 5,732,143 A | 3/1998 | Andrea et al. | |
| 5,825,897 A | 10/1998 | Andrea et al. | |
| 6,061,456 A | 5/2000 | Andrea et al. | |
| 6,151,717 A * | 11/2000 | Lindgren et al. | 2/209 |
| 6,278,786 B1 * | 8/2001 | McIntosh | 381/71.6 |
| 6,738,487 B1 | 5/2004 | Nageno et al. | |

OTHER PUBLICATIONS

Shure E2c-Sound Isolating Earphones, (undated), http://www.amazon.com/Shure-E2c-Sound-Isolating-Earphones/dp/B0000CE1UO.
Shure Inc.—Earphone User Guide, copyrighted 2002, 10 pgs., 27A8809 (B1).

* cited by examiner

*Primary Examiner*—Michael Sherry
*Assistant Examiner*—Terrence R. Willoughby

(57) ABSTRACT

A passive noise reduction apparatus has a headset with at least one ear cup attached to the headset, the ear cup having an ear side and a shell side. An inner shell, having a cup side and an outer side, is mounted to and substantially covers the shell side of the ear cup wherein the cup side of the inner shell faces the shell side of the ear cup. An outer shell, having an inner side and a distal side, is mounted to and substantially covers the inner shell, wherein the inner side of the outer shell is in substantially contiguous contact with the outer side of the inner shell.

18 Claims, 6 Drawing Sheets

SYSTEM AND METHOD FOR PROVIDING PASSIVE NOISE REDUCTION

TECHNICAL FIELD

The present invention is generally related to noise reduction equipment and, more specifically, is related to an apparatus and method for providing passive noise reduction.

BACKGROUND OF THE INVENTION

A number of applications exist for devices that can reduce ambient noise levels for individuals. Many occupations expose employees to high noise levels and, for the protection of employees auditory senses, equipment is required that can reduce the ambient noise levels to which those employees are exposed. In addition, individuals often use headphones while listening to music. The quality of the music listening is enhanced if the headphones utilized are capable of blocking or reducing ambient noise. Further, headsets are regularly used for telecommunication devices. The individuals using telecommunication headsets can communicate more easily if they have a device for blocking out or reducing ambient noise. In addition to the above-mentioned additional applications also exist for devices that can reduce ambient noise levels for individuals.

Headphones and headsets exist in the art that reduce ambient noise levels via use of electrical circuitry. Unfortunately, such manner of ambient noise reduction is costly and not entirely effective. Common passive noise reduction headphone design involves constructing a single hard shell on the earpiece of the headphones. In this design, ambient noise sound waves must permeate the single hard shell. However, sometimes these single hard shells are not capable of blocking out a significant portion of the ambient noise. Ideally, the hard shell design could be augmented to create a more effective passive noise reduction device.

Another problem with existing headphones and headsets, having the passive noise reducing hard shell, is the headphones and headsets are primarily produced with an unimaginative and unoriginal appearance. Most of these devices have a hard, rounded, exterior shell in some variation of black. Part of the problem is that other colors, while more imaginative, are not appropriate for professional settings or are otherwise aesthetically dissatisfying. Ideally, these headphones and headsets could be constructed with a more imaginative and original appearance, while maintaining a style that is aesthetically pleasing and appropriate for a professional setting.

Thus, a heretofore unaddressed need exists in the industry to address the aforementioned deficiencies and inadequacies.

SUMMARY OF THE INVENTION

Embodiments of the present invention provide an apparatus and method for constructing head-mounted passive noise reduction devices.

Briefly described, in architecture, one embodiment of the passive noise reduction apparatus, among others, can be implemented as follows. The passive noise reduction apparatus has a headset with at least one ear cup attached to the headset, the ear cup having an ear side and a shell side. An inner shell, having a cup side and an outer side, is mounted to and substantially covers the shell side of the ear cup wherein the cup side of the inner shell faces the shell side of the ear cup. An outer shell, having an inner side and a distal side, is mounted to and substantially covers the inner shell, wherein the inner side of the outer shell is in substantially contiguous contact with the outer side of the inner shell.

The present invention can also be viewed as providing methods for making a passive noise reduction apparatus. In this regard, one embodiment of such a method, among others, can be broadly summarized by the following steps: forming an ear unit by: mounting an ear cup, having an ear side and a shell side, to an inner shell having a cup side and an outer side, the inner shell substantially covering the shell side of the ear cup wherein the cup side of the inner shell faces the shell side of the ear cup; mounting an outer shell, having an inner side and a distal side, to the inner shell, wherein the inner side of the outer shell is in substantially contiguous contact with the outer side of the inner shell; and connecting at least one ear unit to a headset.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts through several views.

DETAILED DESCRIPTION

Figure 1:
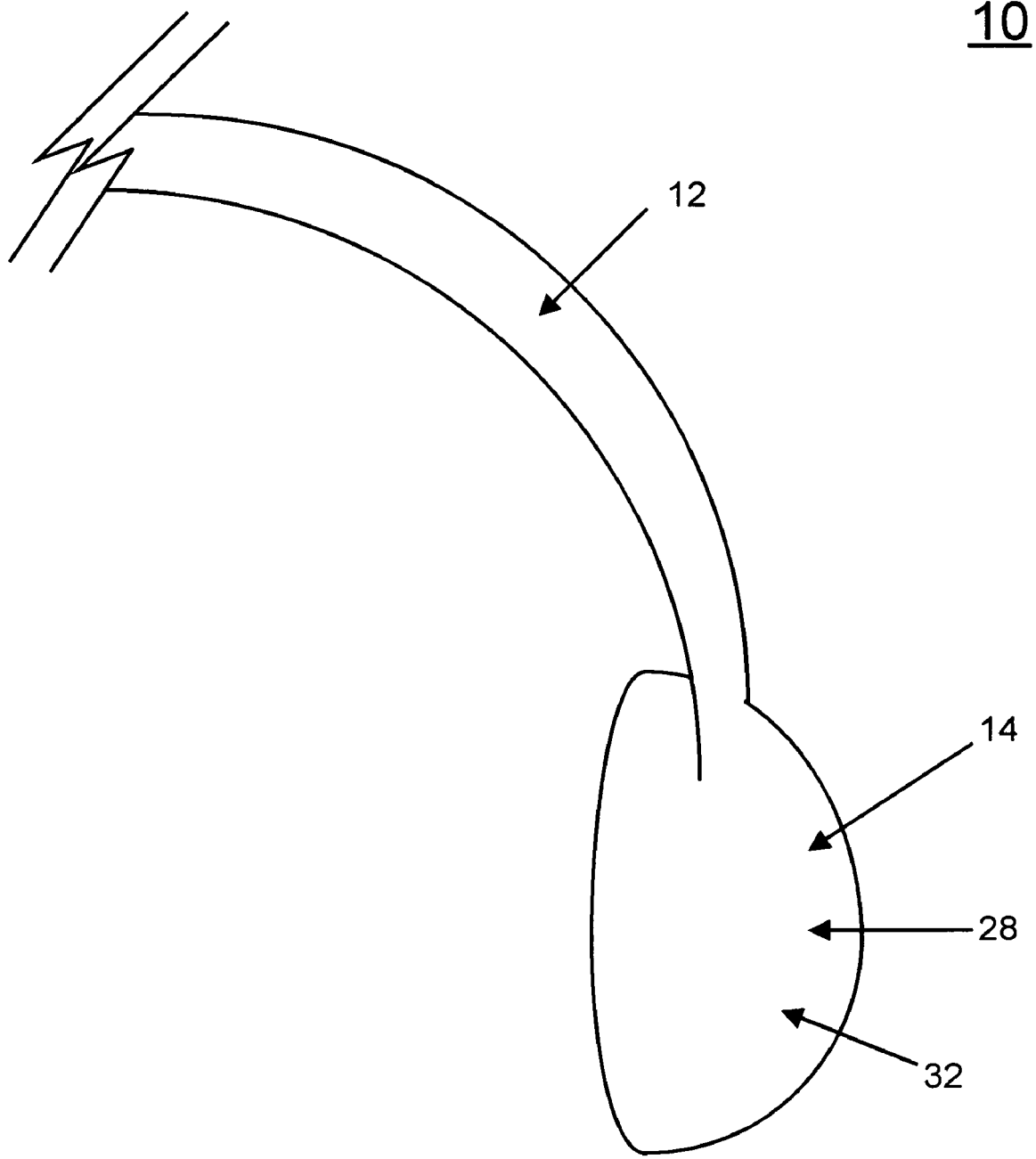
FIG. 1 is a side view of a first exemplary embodiment of the passive noise reduction apparatus.
Figure 2:
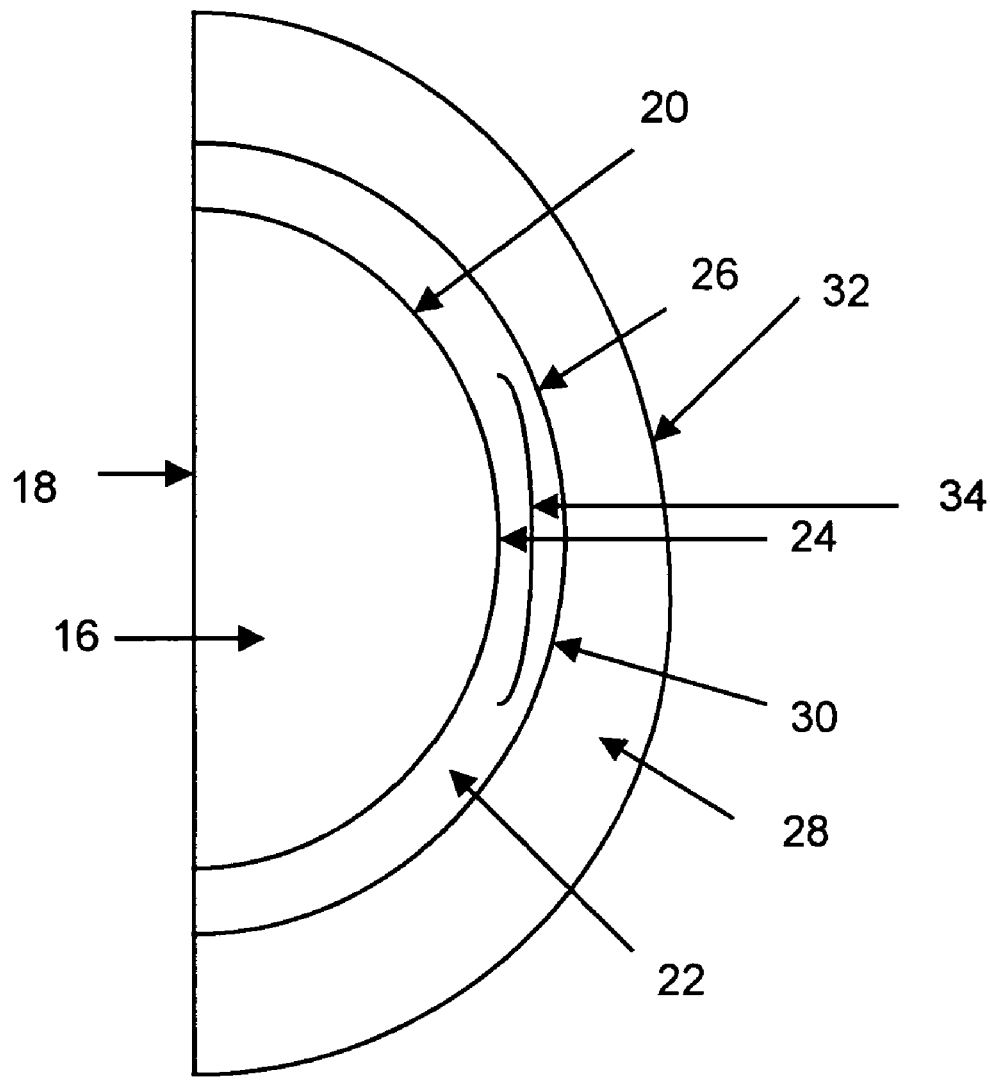
FIG. 2 is a cross-sectional side view of the passive noise reduction apparatus shown in FIG. 1.

A first exemplary embodiment of a passive noise reduction apparatus 10 is shown in FIG. 1 and FIG. 2. The passive noise reduction apparatus 10 includes a headset 12 and at least one ear unit 14 attached to the headset 12. The headset 12 may be designed to have one ear unit 14, as is common in telecommunications applications, or two ear units 14, as would be standard for earphones or ear-protection devices. The ear unit 14 includes an ear cup 16 having an ear side 18 and a shell side 20. The ear unit 14 also includes an inner shell 22 having a cup side 24 and an outer side 26. The inner shell 22 is mounted to and substantially covering the shell side 20 of the ear cup 16 wherein the cup side 24 of the inner shell 22 faces the shell side 20 of the ear cup 16. The ear unit 14 also includes an outer shell 28 having an inner side 30 and a distal side 32. The outer shell 28 is mounted to and substantially covering the inner shell 22, wherein the inner side 30 of the outer shell 28 is in substantially contiguous contact with the outer side 26 of the inner shell 22.

The first exemplary embodiment shown in FIG. 1 and FIG. 2 features a passive noise reduction apparatus 10 that effectively reduces ambient noise for the user of the passive noise reduction apparatus 10 and is cost effective to construct. The use of two shells 22, 28 in the ear unit 14 doubles the level of sound wave impedance featured in single shell devices. The shells 22, 28 are, in some instances, made of plastic and the unique two shell construction offers some interesting, new aesthetic design options for the passive noise reduction apparatus 10.

The passive noise reduction apparatus 10 may be designed such that the inner shell 22 and the outer shell 28 are translucent, thereby permitting an image, engravement, or other type of print, on the shell side 20 of the ear cup 16 to be visible through the inner shell 22 and the outer shell 28. As is mentioned below, the image may instead be located on the inner shell 22 or outer shell 28. The passive noise reduction apparatus 10 may also be designed such that only the outer shell 28 is substantially translucent. If the outer shell 28 is substantially translucent, an image 34 may be located on the inner side 30 of the outer shell 28, whereby the image 34 is visible through the outer shell 28. Or, if the outer shell 28 is substantially translucent, an image 34 may be located on the outer side 26 of the inner shell 22, whereby the image 34 is visible through the outer shell 28. Or, if the outer shell 28 is substantially translucent, the inner shell 22 may be designed to be at least partially translucent, carrying an image 34 or other design visible through the outer shell 28. In any of these designs, the image 34 may be given a three-dimensional appearance through the outer shell 28. It should be noted that other configurations between images, the ear cap 16, the inner shell 22, and the outer shell 28 may be provided.

The passive noise reduction apparatus 10 may be designed to carry electronic devices. The ear cup 16 is generally designed for making comfortable contact with an ear of the wearer. In some designs, the ear cup 16 may carry electronic equipment, such as a speaker. In other designs, such as those where the ear unit 14 is intended to be used for ear-protection, the ear cup 16 may not contain any electronics. When the ear cup 16 is designed with the speaker, the speaker may be hardwired to a device outputting an audio signal or the speaker 36 may receive audio signals wirelessly.

Figure 3:
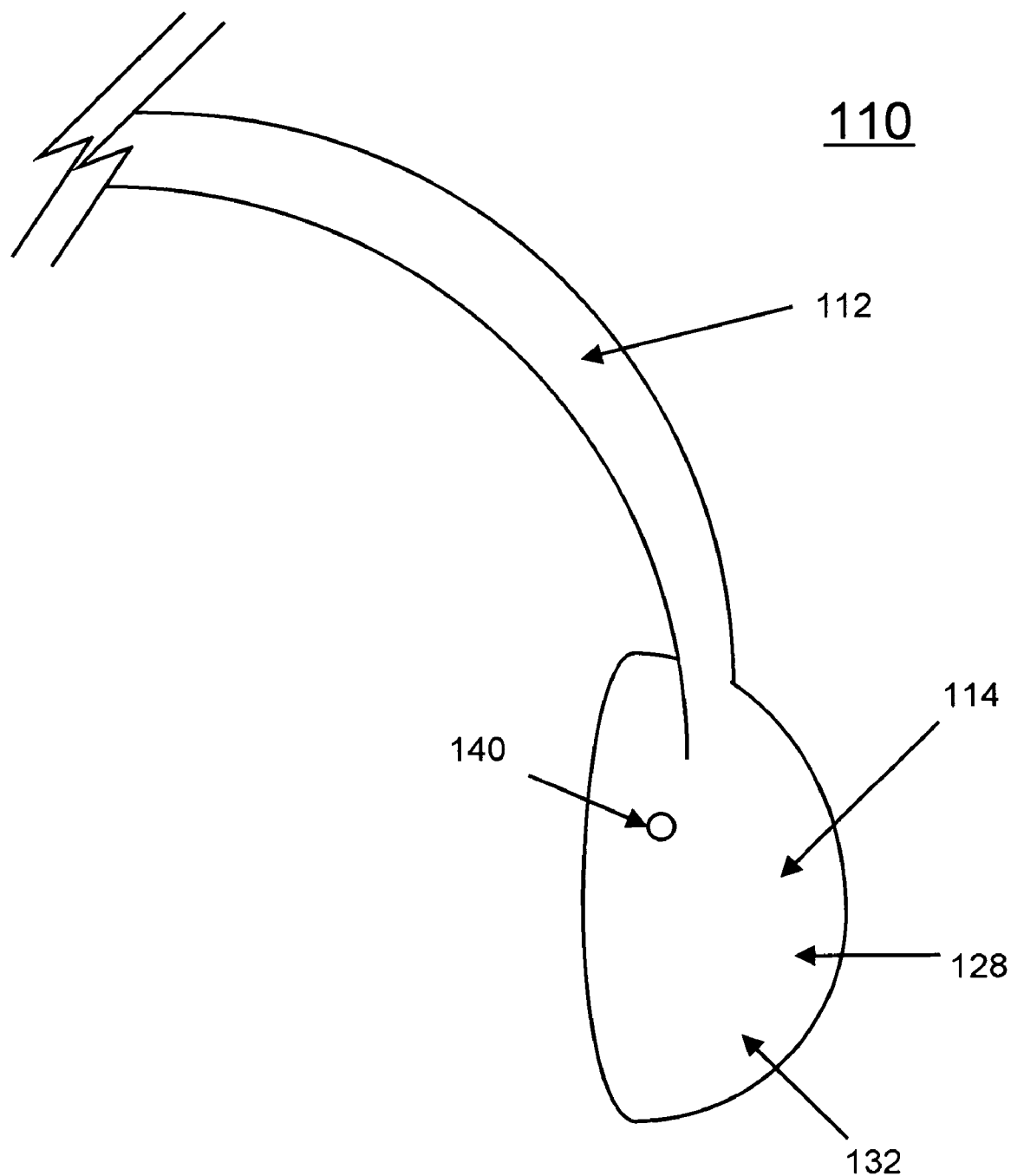
FIG. 3 is a side view of a second exemplary embodiment of the passive noise reduction apparatus.
Figure 4:
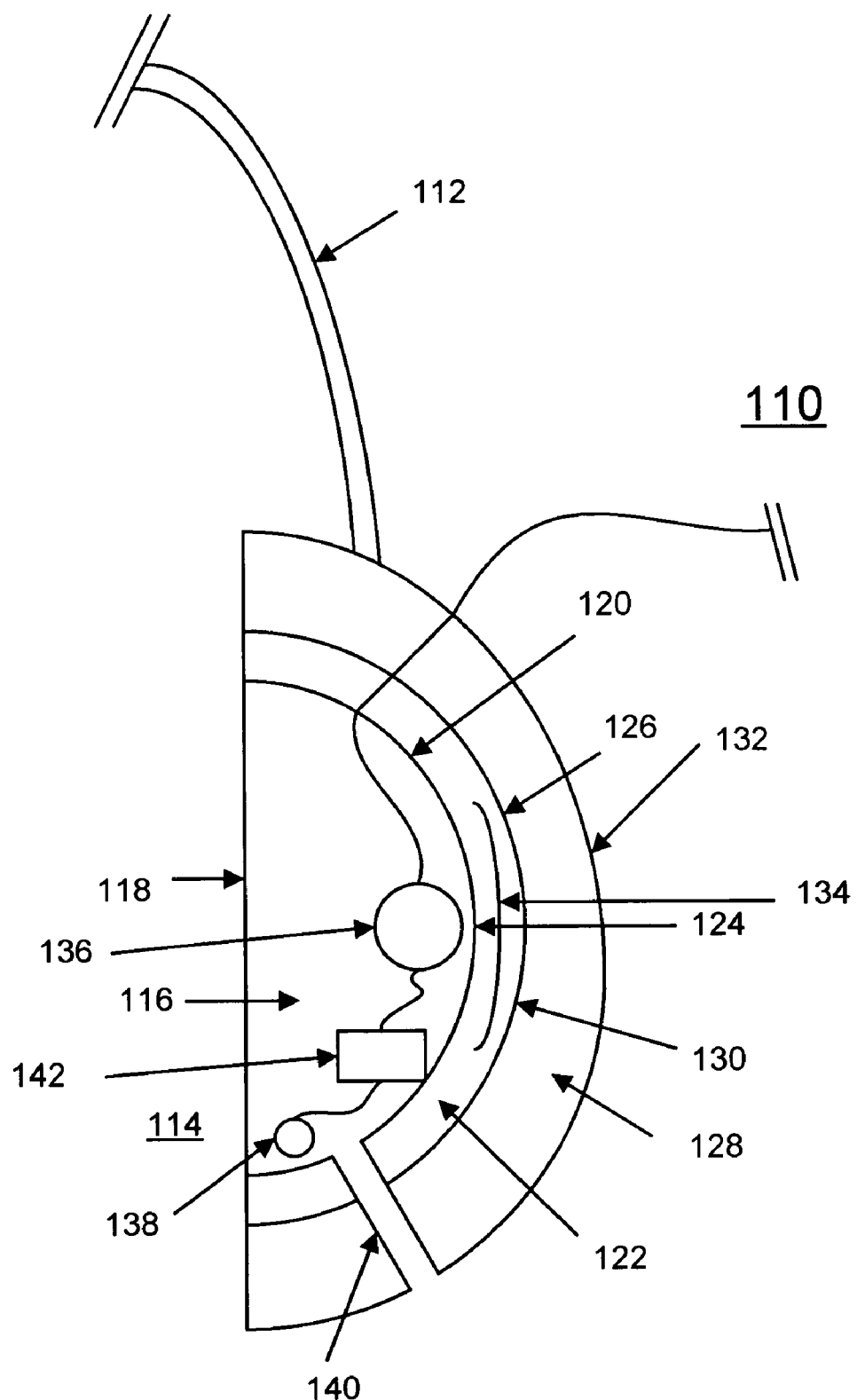
FIG. 4 is a cross-sectional side view of the passive noise reduction apparatus shown in FIG. 3.

The passive noise reduction apparatus 110, in a second exemplary embodiment shown in FIG. 3 and FIG. 4, may also be designed with active noise reduction equipment. The active noise reduction equipment includes a microphone 138 mounted to the ear side 118 of the ear cup 116. An opening 140 is formed through the inner shell 122 and the outer shell 128, in communication with the microphone 138. An active noise reduction circuit 142, electronically connected to the microphone 138 and a speaker 136, receives an ambient noise signal from the microphone 138 and cancels out the ambient noise signal using the speaker 136.

With regards to the second exemplary embodiment, there are a number of prospective techniques for attaching the outer shell 128 to the inner shell 122 and the inner shell 122 to the ear cup 116. The outer shell 128 and the inner shell 122 may be made to be removable from the ear cup 116. The outer shell 128 and the inner shell 122 may be made to be removably connected. Allowing one or more parts of the ear unit 114 to be separable may make it possible for a user of the passive noise reduction apparatus 110 to alter the image 134. Another way to construct the ear unit 114 would be to make the outer shell 128, the inner shell 122, and the ear cup 116 adhesively bonded.

Figure 5:
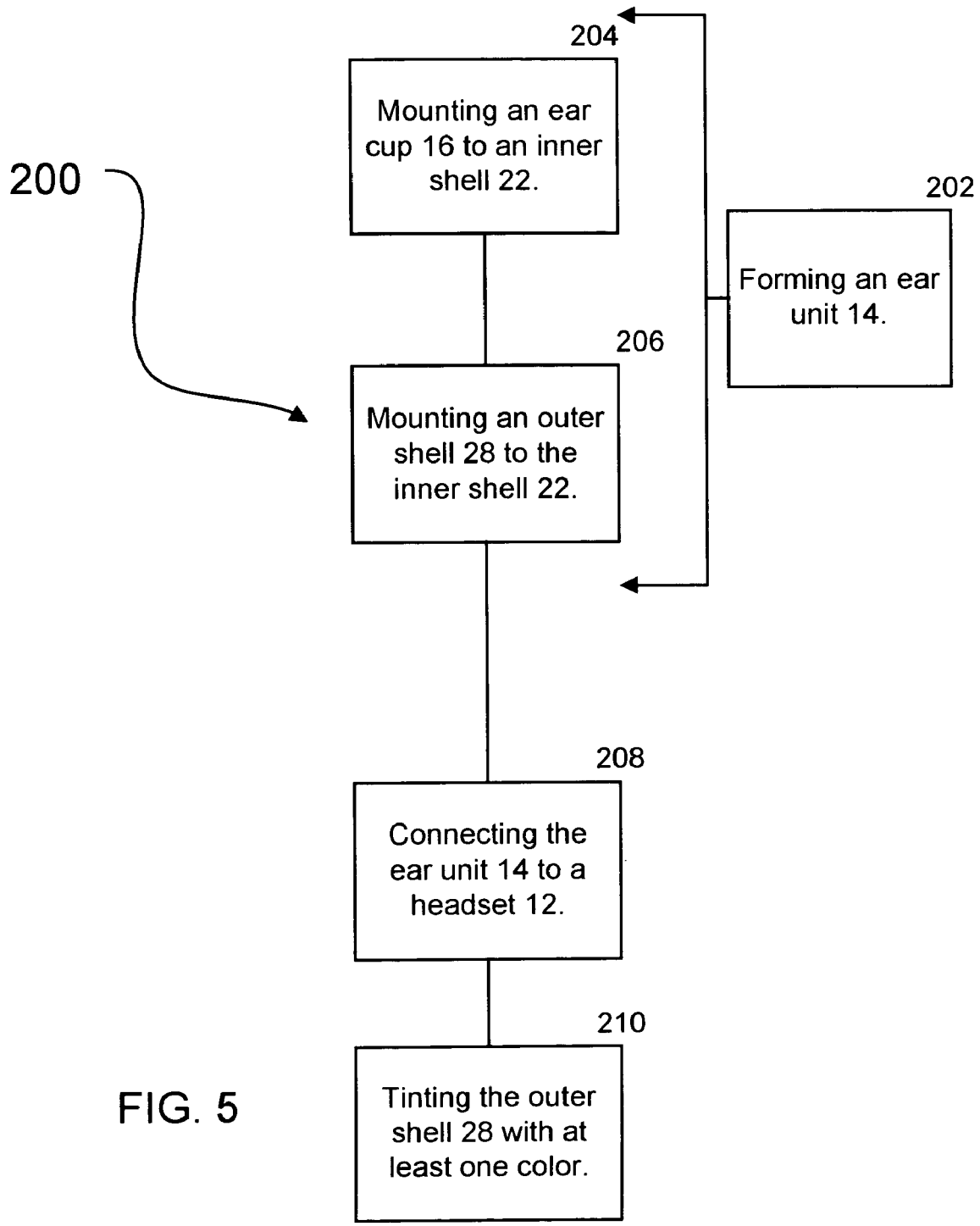
FIG. 5 is a flow chart depicting a method of making the passive noise reduction apparatus shown in FIG. 1 and FIG. 2.
Figure 6:
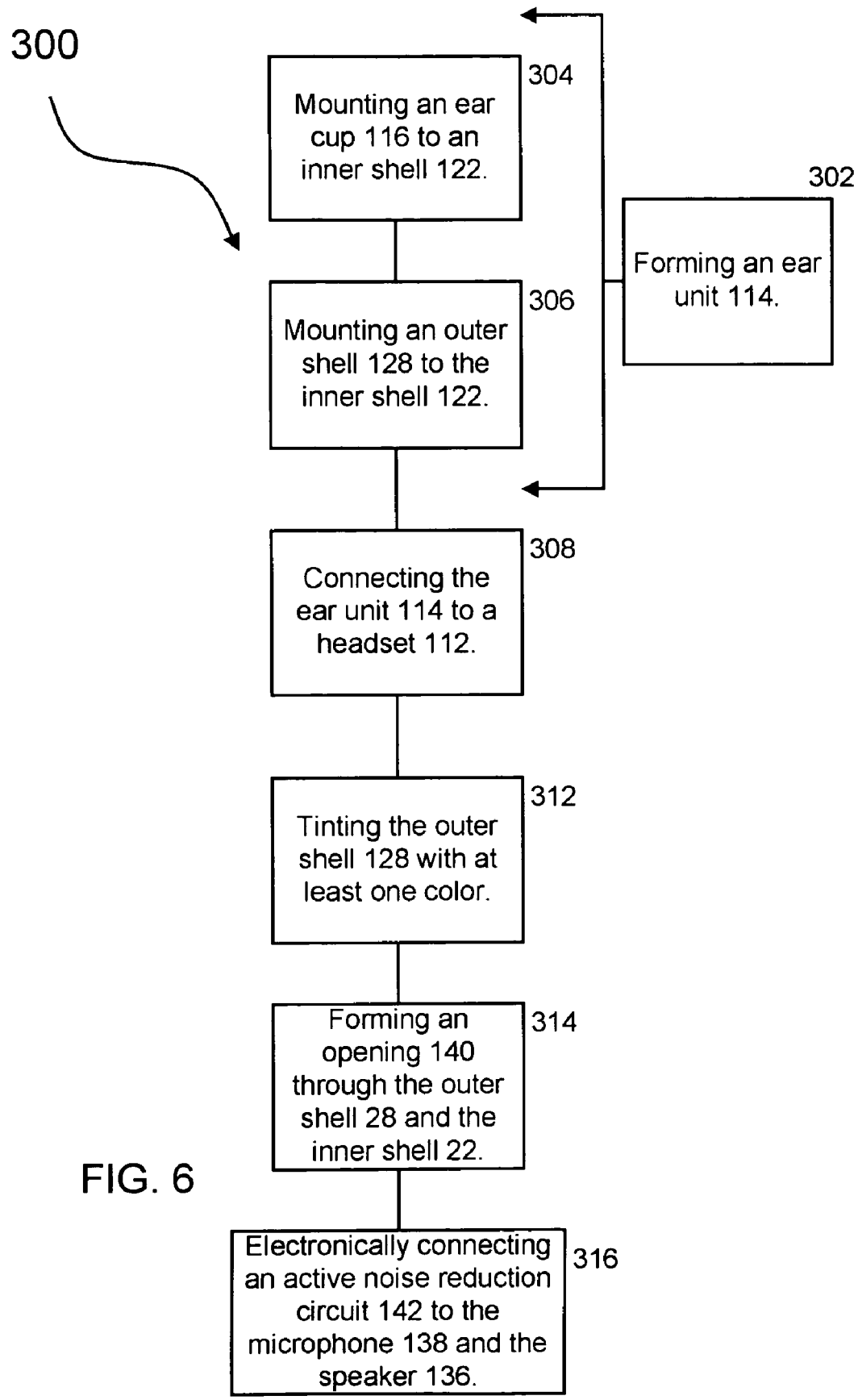
FIG. 6 is a flow chart depicting a method of making the passive noise reduction apparatus shown in FIG. 3 and FIG. 4.

FIG. 5 is a flowchart illustrating the architecture, functionality, and assembly of a possible implementation of the first exemplary embodiment of the passive noise reduction apparatus 10 of FIG. 1 and FIG. 2. FIG. 6 is a flowchart illustrating the architecture, functionality, and assembly of a possible implementation of the second exemplary embodiment of the passive noise reduction apparatus 110 of FIG. 3 and FIG. 4. In this regard, each block represents a module or segment, which comprises one or more executable instructions for assembling the passive noise reduction apparatus 10 and parts thereof. It should also be noted that in some alternative implementations, the functions noted in the blocks may occur out of the order noted in the flow charts. For example, two blocks shown in succession may in fact be executed substantially concurrently or the blocks may sometimes be executed in the reverse order, depending upon the assembly of parts involved, as will be further clarified hereinbelow.

Referring to FIG. 5, the present invention can be viewed as providing a method 200 of making a passive noise reduction apparatus 10. The method 200 shown in FIG. 5 can be utilized to assemble the first exemplary embodiment of the passive noise reduction apparatus 10, as described above. In the method 200, an ear unit 14 is formed (block 202) by first mounting an ear cup 16, having an ear side 18 and a shell side 20, to an inner shell 22 having a cup side 24 and an outer side 26 (block 204). The inner shell 22 substantially covers the shell side 20 of the ear cup 16, wherein the cup side 24 of the inner shell 22 faces the shell side 20 of the ear cup 16. Another step in forming the ear unit 14 (block 202) is mounting an outer shell 28 (block 206), having an inner side 30 and a distal side 32, to the inner shell 22. The inner side 30 of the outer shell 28 is in substantially contiguous contact with the outer side 26 of the inner shell 22. At least one ear unit 14 is connected (block 208) to a headset 12.

The method 200 shown in FIG. 5 contains a number of variations. The step of mounting an outer shell 28 (block 206) to the inner shell 22 may involve removably attaching the outer shell 28 and the inner shell 22. The step of mounting an outer shell 28 (block 206) to the inner shell 22 may involve adhesively attaching the outer shell 28 and the inner shell 22. Alternatively, the outer shell 28 may be fabricated on the inner shell 22. As an example, the outer shell 28 may be molded on the inner shell 22. Of course other methods of fabricating the outer shell 28 on the inner shell 22, may be utilized.

As in the first exemplary embodiment, the inner shell 22 and the outer shell 28 may be constructed from a translucent material, thereby permitting an image 34 on the shell side 20 of the ear cup 16 to be visible through the inner shell 22 and the outer shell 28. Or the outer shell 28 may be translucent, permitting an image 34 mounted in or on the outer shell 28 or on the inner shell 22 to be seen through the outer shell 28, as described in more detail herein. The method 200 may further involve tinting the outer shell 28 (block 210) with at least one color. The inner shell 22 may also be tinted with either the same or a different color than the outer shell 28.

Referring to FIG. 6, the present invention can be viewed as providing a method 300 of making a passive noise reduction apparatus 110. The method 300 shown in FIG. 6 can be utilized to assemble the second exemplary embodiment of the passive noise reduction apparatus 110, as described above. In the method 300, an ear unit 114 is formed (block 302) by first mounting an ear cup 116, having an ear side 118 and a shell side 120, to an inner shell 122 having a cup side 124 and an outer side 126 (block 304). The inner shell 122 substantially covers the shell side 120 of the ear cup 116, wherein the cup side 124 of the inner shell 122 faces the shell side 120 of the ear cup 114. Another step in forming the ear unit 114 (block 302) is mounting an outer shell 128 (block 306), having an inner side 130 and a distal side 132, to the inner shell 122. The inner side 130 of the outer shell 128 is in substantially contiguous contact with the outer side 126 of the inner shell 122. At least one ear unit 114 is connected (block 308) to a headset 112. A microphone 138 and a speaker 136 are mounted to the ear side 118 of the ear cup 116 (block 312). An opening 140 is formed through the inner shell 122 and the outer shell 128 (block 314) and in communication with the microphone 138. The opening 140 may be preformed (block 314) in the shells 122, 128. An active noise reduction circuit 142 is electronically connected to the microphone 138 and the speaker 136 (block 316) to receive an ambient noise signal from the microphone 138 and cancel out the ambient noise signal using the speaker 136.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

We claim:

1. A passive noise reduction apparatus, comprising:
a headset;
at least one ear cup attached to the headset, the ear cup having an ear side and a shell side;
an inner shell having a cup side and an outer side, the inner shell mounted to and substantially covering the shell side of the ear cup wherein the cup side of the inner shell faces the shell side of the ear cup;
an outer shell having an inner side and a distal side, the outer shell mounted to and substantially covering the inner shell, wherein the inner side of the outer shell is in substantially contiguous contact with the outer side of the inner shell;
a speaker mounted within the ear cup;
a microphone mounted to the ear side of the ear cup;
an opening formed through and extending from the inner shell to and through the outer shell and in communication with the microphone; and
an active noise reduction circuit electronically connected to the microphone and the speaker to receive an ambient noise signal from the microphone and cancel out the ambient noise signal using the speaker.

2. The passive noise reduction apparatus of claim 1, wherein the inner shell and the outer shell are translucent, thereby permitting an image on the shell side of the ear cup to be visible through the inner shell and the outer shell.

3. The passive noise reduction apparatus of claim 1, wherein the outer shell is substantially translucent.

4. The passive noise reduction apparatus of claim 3, further comprising an image located on the inner shell of the outer shell, whereby the image is visible through the outer shell.

5. The passive noise reduction apparatus of claim 3, further comprising an image located on the outer side of the inner shell whereby the image is visible through the outer shell.

6. The passive noise reduction apparatus of claim 3, wherein the inner shell is substantially translucent.

7. The passive noise reduction apparatus of claim 1, wherein the outer shell and the inner shell are removable from the ear cup.

8. The passive noise reduction apparatus of claim 1, wherein the outer shell and the inner shell are adhesively attached.

9. The passive noise reduction apparatus of claim 1, wherein the outer shell and the inner shell are removably attached.

10. A method of making a passive noise reduction apparatus, said method comprising the steps of:
forming an ear unit by:
mounting an ear cup, having an ear side and a shell side, to an inner shell having a cup side and an outer side, the inner shell substantially covering the shell side of the ear cup wherein the cup side of the inner shell faces the shell side of the ear cup;
mounting an outer shell, having an inner side and a distal side, to the inner shell, wherein the inner side of the outer shell is in substantially contiguous contact with the outer side of the inner shell;
connecting at least one ear unit to a headset;
mounting a microphone to the ear side of the ear cup;
mounting a speaker to the ear side of the ear cup;
forming an opening through and extending from the inner shell to and through the outer shell and in communication with the microphone; and
electronically connecting an active noise reduction circuit to the microphone and the speaker to receive an ambient noise signal from the microphone and cancel out the ambient noise signal using the speaker.

11. The method of claim 10, wherein the outer shell and the inner shell are removably attached.

12. The method of claim 10, wherein the inner shell and the outer shell are translucent, thereby permitting an image on the shell side of the ear cup to be visible through the inner shell and the outer shell.

13. The method of claim 10, wherein the outer shell is substantially translucent.

14. The method of claim 13, further comprising the step of fixing an image to the inner side of the outer shell, whereby the image is visible through the outer shell.

15. The method of claim 13, further comprising the step of fixing an image to the outer side of the inner shell, whereby the image is visible through the outer shell.

16. The method of claim 13, further comprising the step of tinting the outer shell with at least one color.

17. The method of claim 10, wherein the step of mounting the outer shell to the inner shell further comprising adhesively mounting the outer shell to the inner shell.

18. A passive noise reduction apparatus, comprising:
a headset;
at least one ear cup attached to the headset, the ear cup having an ear side and a shell side;
an inner shell having a cup side and an outer side, the inner shell mounted to and substantially covering the shell side of the ear cup wherein the cup side of the inner shell faces the shell side of the ear cup;
an outer side having an inner side and a distal side, the outer shell fabricated on and substantially covering the inner side, wherein the inner side of the outer shell is in substantially contiguous contact with the outer side of the inner shell, wherein the outer shell is substantially translucent;

a speaker mounted within the ear cup;

a microphone mounted to the ear side of the ear cup;

an opening formed through and extending from the inner shell to and through the outer shell and in communication with the microphone; and an active noise reduction circuit electronically connected to the microphone and the speaker to receive an ambient noise signal from the microphone and cancel out the ambient noise signal using the speaker.

* * * * *